United States Patent [19]

Holubka

[11] 4,423,171

[45] * Dec. 27, 1983

[54] TERTIARY ALCOHOL-DIBLOCKED DIISOCYANATE DIUREA OLIGOMERS AND COATING COMPOSITIONS COMPRISING SAME

[75] Inventor: Joseph W. Holubka, Livonia, Mich.

[73] Assignee: Ford Motor Company, Dearborn, Mich.

[*] Notice: The portion of the term of this patent subsequent to Aug. 2, 2000, has been disclaimed.

[21] Appl. No.: 334,792

[22] Filed: Dec. 28, 1981

[51] Int. Cl.$^3$ .................. C08G 18/28; C08K 5/05; C08K 5/07; C08L 63/00

[52] U.S. Cl. .................. 523/454; 523/400; 523/456; 524/361; 524/379; 524/589; 525/528; 528/45

[58] Field of Search ............ 523/400, 454, 456; 524/379, 361, 589; 525/528; 528/45

[56] References Cited

U.S. PATENT DOCUMENTS

| | | | |
|---|---|---|---|
| 2,511,544 | 6/1950 | Rinke et al. | 528/85 |
| 3,245,961 | 4/1966 | Feischer et al. | 528/45 |
| 3,779,994 | 12/1973 | Wood | 528/71 |
| 3,931,115 | 1/1976 | Strassel | 528/64 |
| 3,931,116 | 1/1976 | Bernstein et al. | 528/49 |
| 3,939,126 | 2/1976 | Carder et al. | 528/75 |
| 4,031,050 | 6/1977 | Jerabek | 525/528 |
| 4,036,906 | 7/1977 | Finelli | 528/61 |
| 4,111,917 | 9/1978 | Larsen | 525/528 |
| 4,134,866 | 1/1979 | Tominaga et al. | 528/45 |
| 4,192,932 | 3/1980 | Dickie et al. | 525/511 |
| 4,239,878 | 12/1980 | Kobayashi et al. | 528/45 |
| 4,338,423 | 7/1982 | Holubka | 525/511 |

FOREIGN PATENT DOCUMENTS 709288  5/1954  United Kingdom .................. 528/45

*Primary Examiner*—Ronald W. Griffin
*Attorney, Agent, or Firm*—Peter D. McDermott; Roger L. May

[57] ABSTRACT

This invention provides polymer forming resin systems and high solids solvent based chain-extendable, crosslinkable coating compositions comprising same. The invention comprises a polyepoxide, preferably a diepoxide, of molecular weight between about 100 and about 1000 used generally in amounts from about 10% to about 50% by weight of total resin, and novel diblocked diisocyanate diurea oligomers of molecular weight between about 300 and about 5000. The resin components provide chain-extension polymerization during cure at elevated temperature, in situ, on the surface of a substrate. The resin system is self-crosslinking. That is, no additional crosslinking component is required. The cured coatings of the invention provide greatly improved physical properties, in particular greatly improved corrosion resistance.

37 Claims, No Drawings

TERTIARY ALCOHOL-DIBLOCKED DIISOCYANATE DIUREA OLIGOMERS AND COATING COMPOSITIONS COMPRISING SAME

INTRODUCTION

This invention relates to novel resin systems and to high solids, solvent based coating compositions comprising same. A first component comprises any of certain novel chain-extendable, crosslinkable tertiary alcohol-diblocked diisocyanate diurea oligomers. The second comprises polyepoxide. The resin components provide crosslinking and chain-extension polymerization during cure at elevated temperature, in situ, on the surface of a substrate. The resin system is self-crosslinking, that is, no additional crosslinking agent is required. The cured coatings of the invention are highly humidity and solvent resistant and provide exceptional corrosion resistance.

RELATED APPLICATIONS

This application is related to concurrently filed application Ser. No. 334,794, filed Dec. 28, 1981, entitled Novel Diblocked Diisocyanate Urea Urethane Oligomers and Coating Compositions Comprising Same; Ser. No. 334,842, filed Dec. 28, 1981, entitled Novel Diblocked Diisocyanate Diurea Oligomers and Coating Compositions Comprising Same; and Ser. No. 334,793, filed Dec. 28, 1981, entitled Novel Tertiary Alcohol-Diblocked Diisocyanate Urea Urethane Oligomers and Coating Compositions Comprising Same.

BACKGROUND OF THE INVENTION

Solvent based coating compositions are known which employ high molecular weight (e.g. 2,000 to 10,000) polymer resins having crosslinking functionality, and a suitable crosslinking agent. Typically, such coating compositions are applied to a substrate, for example, by spraying, and are then cured by baking the coated substrate at an elevated temperature suitable to drive off the organic solvent and to promote the crosslinking reaction. The resulting thermoset coating, if sufficiently humidity, solvent and corrosion resistant, can provide aesthetic and functional advantages including corrosion protection for the underlying substrate.

Coating compositions comprising such high molecular weight polymer resins typically comprise only 25% to 50% solids so as to be sprayable or otherwise conveniently applicable to a substrate. The viscosity of coating compositions of higher solids content is typically too high for this purpose. Conventional epoxy ester based automotive vehicle spray primers, for example, typically have a volatile organic content ("VOC") of approximately 540 g/l.

Elimination of the volatile organic solvent portion during curing of these conventional low-solids coating compositions presents toxicity and in some cases flammability hazards. Furthermore, bulk volume of these coating compositions is relatively large and therefore presents undesirable material handling difficulties, and added expense. Furthermore, excessive solvent losses and/or solvent recovery equipment add considerable expense to the coating operation. Recently, governmental regulations on hydrocarbon emissions, particularly applicable to automotive coating operations, mandate a significant reduction in volatile organic content for coating compositions. Thus, for example, govermental guidelines for 1982 presently require that emissions of volatile organics from automotive vehicle primer coating operations be reduced to that equivalent to using coating compositions of no greater than 350 g/l (2.9 lb./gal) VOC. To meet government guidelines coating compositions of VOC greater than 350 g/l can be employed in conjunction with emissions treatment equipment to achieve the specified emissions limit. Such treatment equipment presents significant additional expense, however, and thus there is a great need to provide coating compositions of VOC reduced near to, or preferably even lower than, the 350 g/l governmental limit.

In response to these concerns, high solids coating compositions have been suggested which, typically, employ low molecular weight multi-functional adducts or copolymers in combination with multi-functional crosslinking agents. These high solids coating compositions are less viscous and, therefore, can be applied by spraying, for example, with far lower VOC than was possible with conventional epoxy ester based coating compositions or other conventional coating compositions comprising high molecular weight polymer resins. After application to the substrate, high solids coating compositions are cured by baking at a cure temperature, that is, at an elevated temperature suitable to drive off the volatile organic content and to promote polymerization and crosslinking of the multi-functional low molecular weight component(s).

Typically, high solids coating compositions yield cured coatings having polymeric networks that differ significantly in structure and morphology from the polymeric networks provided by conventional, low solids coating compositions comprising high molecular weight polymers. Consequently, the physical properties of the coatings provided by such high solids coatings compositions can differ significantly from those of the cured coatings provided by the conventional, low solids coating compositions. In particular, the cured coatings obtained from known high solids coating compositions can be inferior in that they can be less flexible, less solvent resistant, less adherent to the substrate and/or for other reasons provide less corrosion inhibition for the underlying substrates. Accordingly, it would be highly desirable to provide a coating composition comprising low molecular weight materials suitable for use in high solids, solvent based coating compositions and yet which, upon curing, form coatings having physical properties, particularly corrosion resistance, comparable to or better than the physical properties of coatings obtained from conventional low solids solvent based coating compositions.

Accordingly, it is an object of the present invention to provide novel resin compositions suitable for use in resin compositions suitable for use in high solids, solvent-based coating compositions. In this regard, it is a particular object of the invention to provide novel coating compositions which are curable by chain-extension and crosslinking during cure, in situ, on the surface of a substrate to form polymeric coatings similar in properties to those obtainable through use of conventional low solids, solvent-based coatng compositions.

It is a particular object of the invention to provide a coating composition of sufficiently low VOC to facilitate compliance with governmental guidelines. It is also an object of the invention to provide such a coating composition which can be applied to a substrate by spraying or other known method.

It is another object of the invention to provide a method of making a coating on a substrate, which coating has advantageous physical properties including humidity, solvent and corrosion resistance. Additional aspects and advantageous of the invention will be apparent from the following description thereof.

SUMMARY OF THE INVENTION

According to the present invention, low molecular weight chain-extendable, crosslinkable tertiary alcohol-diblocked diisocyanate diurea oligomers are provided which are suitable for use in high solids, organic solvent based coating compositions. The novel oligomers of the invention preferably have a number average molecular weight of about 300 to about 5000, more preferably about 300 to about 1500, and are the reaction product of half-blocked diisocyanate with suitable diamine. The half-blocked diisocyanate is the reaction product of organic diisocyanate with a tertiary alcohol blocking agent.

According to another aspect of the invention, a novel solvent-based resin composition comprises the novel chain-extendable, crosslinkable tertiary alcohol diblocked diisocyanate diurea oligomer of the invention, polyepoxide bearing preferably about 2 to 10, more preferably about 2 to 4 epoxide groups, and having molecular weight of about 100 to 1000, more preferably about 300 to 700, and suitable organic solvent. The resin composition comprises latent amine chain-extension polymerization functionality and undergoes both chain-extension polymerization and crosslinking reaction, in situ, on the surface of the substrate during cure of the coating composition to form high molecular weight polymers. More specifically, the two tertiary alcohol-blocked isocyanate groups of the novel oligomer of the invention undergo thermal decomposition at elevated temperature of about 80° to about 220° to afford an amine functional oligomer product, volatile alkene and carbon dioxide. Following such decomposition, the resulting amine functional oligomer product reacts with the epoxy functionality of the polyepoxide of the coating composition. That is, during cure of the coating composition, in situ, on the surface of the substrate, the amine functionality generated by the decomposition of the tertiary alcohol-blocked isocyanate groups will provide chain-extension and crosslinking reactions with the epoxy groups of the polyepoxide component of the coating composition. Where the polyepoxide bears three or more epoxy groups, the coating composition, during cure, provides a high degree of chain extension polymerization and the cured coating has a high crosslink density. Where all or a substantial portion of the polyepoxide is diepoxide, the coating composition, during cure, provides a substantially higher degree of chain-extension and the cured coating has a substantially lower crosslink density.

The resin composition of the invention can be formulated into high solids coating compositions having a viscosity as low as about 40 seconds or less, #4 Ford Cup, at 27° C., at calculated VOC of about 400 g/l or less.

According to another aspect of the invention, a method of making a corrosion, solvent and humidity resistant coating on a substrate comprises applying to the substrate the novel thermosetting resin composition of the invention and heating the resin composition to between about 80° C. and about 220° C. and preferably to between about 110° C. and about 180° C. for a period sufficient to yield a cured coating. The cured coating, which is yet another aspect of the invention, is solvent and humidity resistant and has been found to provide exceptionally good corrosion resistance.

DETAILED DESCRIPTION OF THE INVENTION

As used herein, a high solids coating composition is one comprising polymerizable resin in which a volatile organic solvent content of about 400 g/l (3.4 lb./gal.) or less yields a viscosity of less than approximately 40 sec. #4 Ford Cup at 27° C. (80° F.). Thus, such high solids coating composition could be applied, for example, by spray techniques, to a substrate.

The novel crosslinkable, chain-extendable diblocked diisocyanate diurea oligomer of the invention preferably has a number average molecular weight of about 300 to about 5000, more preferably about 300 to about 1500. These oligomers are provided as the reaction product of a suitable diamine with suitable tertiary alcohol half-blocked diisocyanate. The two amine groups of the diamine each react with the free isocyanate functionality of a different half-blocked diisocyanate molecule, each forming a urea linkage. The reaction product comprises two blocked isocyanate groups, one from each of the two half-blocked diisocyanate molecules which reacted with the diamine. The diamine and half-blocked diisocyanate are reacted together in molar ratio of about 1:2, respectively, according to methods which are well known to the skilled of the art.

It will be within the skill of the art in view of the present disclosure to select a suitable diamine, of which many, including aromatic and aliphatic diamines, are readily commercially available. Preferred aliphatic diamines are of molecular weight about 50 to about 700, more preferably about 50 to about 300 and include, for example, alkylenediamines, wherein the alkylene moiety is straight or branched chain and has, preferably about 2 to about 20, more preferably about 3 to about 12 carbons, and of which terminal alkylenediamines, that is, alkylenediamines bearing two terminal amine functionality, are most preferred, for example, 1,6-hexanediamine, 1,5-pentanediamine, 1,4-butanediamine and a mixture of any of them. Also preferred are cycloaliphatic diamines of about 4 to about 20 carbons, for example, isophorone diamine, and aromatic diamines wherein each amine is substituted on the same benzene ring or on different benzene rings linked through a covalent bond or through one or more carbons of a one to seven carbon aliphatic moiety, for example, toluene diamine and 4,4'-methlenedianiline.

Suitable half-blocked organic diisocyanate has a number average molecular weight of about 120 to about 2000, preferably about 120 to about 600 and comprises the reaction product of a suitable organic diisocyanate with suitable monofunctional tertiary alcohol blocking agent in approximately 1:1 molar ratio. Suitable organic diisocyanates are readily commercially available and include many known to the skilled of the art. Suitable organic diisocyanates include aromatic diisocyanates, for example, phenylene diisocyanates and toluene diisocyanates, and aliphatic diisocyanates, for example, isophorone and diisocyanates and diisocyanatoalkane wherein the alkyl moiety has preferably about three to about ten carbons, for example, 1,4-diisocyanatobutane and 1,6-diisocyanatohexane, and the like or a compatible mixture of any of them. Most preferably the organic diisocyanate has a molecular weight less than about 250.

For lower temperature curing resin composition, it generally will be preferred that the diisocyanate be an aromatic diisocyanate, since the thermal decomposition temperature of tertiary alcohol-blocked aromatic isocyanate functionality is typically significantly lower than of tertiary alcohol-blocked aliphatic isocyanate functionality. Accordingly, those resin compositions of the invention comprising tertiary alcohol-diblocked aromatic diisocyanate diurea oligomers cure at substantially lower temperature, for example, as low as 80° C. in preferred embodiments. Geneally, it will be preferred that the organic diisocyanate be selected such that the blocked isocyanate group will remain blocked for long periods of time at normal storage temperatures, but will be substantially totally "de-blocked" at elevated "cure" temperature. It will be within the skill of those skilled in the art in view of the present disclosure to select a suitable oragnic diisocyanate to provide de-blocking temperatures meeting the requirements of each particular application intended for a coating composition of the invention. It will be preferred, generally, that the organic diisocyanate be selected such that the blocked isocyanate functionality of the diblocked diisocyanate diurea oligomer of the invention will undergo thermal decomposition (i.e., that the coating composition be curable) at a temperature within the range of about 110° C. to about 180° C.

Suitable half-blocked diisocyanate is prepared by reaction of any suitable organic diisocyanate, as described above, with sufficient monofunctional tertiary alcohol blocking agent to block approximately one half of the isocyanate functionality. Accordingly, monofunctional tertiary alcohol blocking agent is reacted with organic diisocyanate in approximately 1:1 molar equivalent ratio. Suitable techniques well known to the skilled of the art can be employed to maximize the yield of half-blocked diisocyanate, such as, for example, adding the blocking agent slowly to the organic diisocyanate under reaction conditions. The half-blocked diisocyanate is then reacted with the previously described diamine in molar ratio of about 2:1, respectively, to produce the chain-extendable, crosslinkable diblocked diisocyanate diurea oligomer or the invention.

Suitable reaadily commercially available monofunctional tertiary alcohol blocking agents, that is, alcohols bearing a tertiary hydroxyl group, are well known to the skilled of the art. Preferred monofunctional blocking agent include, for example, those of lower molecular weight, since the blocking agent is lost from the coating composition during the curing process and then comprises curing process emissions. Accordingly, blocking agents of 4 to about 20 carbons, more preferably 4 to about 6 carbons, for example, t-butyl alcohol, which is most preferred in view of its lower cost and commercial availability, 2-methyl-2-hydroxy butane, 2-methyl-2-hydroxypentane, 2-methyl-2-hydroxyhexane, or cyclic tertiary alcohols, for example, 1-methylcyclohexanol and the like or a mixture of any of them.

The novel solvent based resin compositions of the invention comprise the novel chain-extendable crosslinkable tertiary alcohol-diblocked diisocyanate diurea oligomers of the invention and suitable polyepoxide. Preferred polyepoxides have from 2 to about 10 epoxide groups, more preferably from 2 to about 4. Preferably the polyepoxide (or each of them) has a number average molecular weight between about 100 and 1000, and more preferably between about 300 and 700. Numerous suitable polyepoxides are readily commercially available and will be apparent to the skilled of the art in view of the present disclosure. Preferred polyepoxides include, for example, any of the wide variety of acyclic or cyclic aliphatic polyepoxides such as, for example, 1,4-butane diol diglycidyl ether, vinylcyclohexene diepoxide and Araldite Cy 179 (trademark, Ciba-Geigy Corporation, Ardsley, N.Y.) and aromatic polyepoxides, such as, for example Bisphenol A epichlorohydrin epoxy resins and the like or a compatible mixture of any of them. Preferred polyepoxides include terminal polyepoxides, that is, polyepoxides bearing two terminal epoxide functionality, since these are generally more reactive and therefore provide coating compositions which cure faster and/or at lower temperature.

Preferred polyepoxides also include diepoxides. Most preferred in view of their commercial availability are, for example, acyclic and cyclic aliphatic diepoxides such as, for example, 1,4-butanediol diglycidyl ether and 4-vinylcyclohexene dioxide and aromatic diepoxides such as, for example, Bisphenol A epichlorohydrin epoxy resins, for example, Epon 828 and other members of the Epon (trademark) series, Shell Chemical Company, Houston, Tex., and DER 331 (trademark) and other members of the DER (trademark) series, Dow Chemical Company, Midland, Mich. Also preferred are cycloaliphatic diepoxy resins, for example, the Eponex (trademark) series of Shell Chemical Company, Houston, Tex., hydantoin epoxy resins, for example, Resin XB2793 (trademark), Ciba-Geigy Corporation, Ardsley, N.Y. and epoxy novalak resins such as, for example, Epon 152 (trademark) and Epon 154 (trademark) of Shell Chemical Company.

In general, of the above described diepoxides, the lower molecular weight diepoxides are preferred, for example, Epon 828 (trademark), since a resin composition of correspondingly lower viscosity (or lower VOC) is provided. Other, higher molecular weight diepoxides, for example, higher molecular weight members of the Epon (trademark) series, are suitable for coating compositions of somewhat higher viscosity (or lower solids content).

The higher molecular weight members of the Epon series, for example Epon 1001 and Epon 1004, may be somewhat less preferred, since they afford coating compositions of higher VOC (or lower solids content). Also, however, improved properties, for example, improved corrosion resistance have been achieved with coating compositions comprising prepared using such materials and the choice of suitable polyepoxide will depend upon the particular application intended for the coating composition.

Polyepoxide can be used in approximately stoichiometric amount in the coating composition. That is, the coating composition can comprise polyepoxide and tertiary alcohol-diblocked diisocyanate diurea oligomer in weight ratio of about 1:1 to about 1:10, more preferably about 1:1 to about 1:2, respectively. Such composition provides efficient chain-extension polymerization during cure of the coating composition.

Network crosslink density can be controlled, and therefore the flexiblity and other properties of the cured coating can to a large extent be controlled by selection of the molecular weight of the polyepoxide and of the tertiary alcohol-diblocked diisocyanate diurea oligomer used in the coating composition. Crosslink density increases and flexibility decreases as the epoxide equivalent weight of the polyepoxide is reduced and/or as the isocyanate equivalent weight of the diblocked diisocyanate diurea oligomer is reduced. Thus, it will be apparent to the skilled of the art in view of the present disclosure that the selection of the polyepoxide and the selection of the organic diisocyanate, blocking agent and diamine reactants for preparing the diblocked diisocyanate diurea oligomer provides substantial control of the crosslink density in the cured coating. Thus, for example, if the diamine used is 1,4-butanediamine, there will be a higher crosslink density in the cured coating than if, for example, 1,10-decanediamine is used. Lower molecular weight aliphatic diamines, those of one to six carbons, for example, ethylenediamine and hexanediamine, are preferred over aromatic diamines if providing a very high solids content (that is, low VOC) coatng composition is of primary concern. The lowest molecular weight aromatic diamines, for example, toluene diamine, have seven or more carbons and require a greater VOC for any desired viscosity.

It has been found that those oligomers of the invention comprising tertiary alcohol-blocked aliphatic isocyanate moieties are more stable and require higher cure temperatures than those oligomers comprising tertiary alcohol-blocked aromatic isocyanate moieties. Accordingly, cure temperatures of about 110° C. to about 220° C., more typically about 150° C. to about 180° C. are required for resin systems of the invention employing oligomers comprising blocked aliphatic isocyanate moieties, while temperatures of only about 60° C. to about 150° C., more typically about 80° C. to about 130° C. are required for those employing oligomers comrpising blocked aromatic isocyanate moieties.

Sufficient solvent is used in the coating composition of the invention to reduce the viscosity of the coating composition to a level suitable for application to the substrate in the desired manner. The molecular weight of the polyepoxide and of the tertiary alcohol-diblocked diisocyanate diurea oligomer will affect the volatile organic content of the coating composition at a desired viscosity. Where a high-solids coating composition is desired, preferably lower molecular weight components are employed, since this can provide high-solids coating compositions which can be applied easily to a substrate by spray or other means in a coating composition having a calculated volatile organic content of as low as about 350 g/l to 400 g/l (2.9 lb./gal. to 3.4 lb./gal.) or less. More specifically, while conventional epoxy ester-type automotive spray-applied primer coating compositions are known to require a volatile organic content of about 540 g/l, the novel coating compositions of the present invention have been found to require as little as about 350 g/l to 400 g/l (2.9 lb./gal. to 3.4 lb./gal.) or less VOC (calculated) to provide a viscosity of less than about 40 sec., #4 Ford Cup at 27° C. (80° F.). Of course, the coating compositions of the invention need not be formulated as a "high solids" composition, but rather can have a higher VOC to provide a lower viscosity. It is generally preferred in automotive vehicle spray coating applications and the like, for example, that sufficient solvent be used to provide a viscosity of about 15 to 40 sec., #4 Ford Cup at 27° C. (80° F.).

It will be within the skill of the art to determine the proper volatile organic content for a given coating composition of the invention for a given application. In general, suitable solvents include, for example, Cellosolve (trademark), Butyl Cellosolve (trademark), Butyl Cellosolve Acetate (trademark), Hexyl Cellosolve (trademark), Hexyl Cellosolve Acetate (trademark), Proposol P (trademark), Proposol B (trademark), Propsol M (trademark), all of Union Carbide Corporation, New York, N.Y., butanol, methyl ethyl ketone, methyl amyl ketone and the like, or a compatible mixture of any of them. Additional suitable solvents will be apparent to the skilled of the art in view of the present disclosure.

Any solvent allowed to remain in the cured coating should be inert so as to avoid adverse effect upon the cured coating or upon another coating used in conjunction with it during the curing process or thereafter. Preferably the cured coating is completely free of solvent. The preferred solvents, in addition, have relatively low volatility at temperatures appreciably below their boiling point such that solvent evaporation is low during storage and/or application of the coating composition to the substrate.

Also preferably included in the coating composition of the invention is any of a variety of commercially available catalysts which, in view of the present disclosure, will be apparent to the skilled of the art to be suitable to catalyze epoxy/amine reaction. Suitable catalysts include, for example, dibutyl tin dilaurate.

In addition, flow control agent, for example, polybutyl acrylate; wetting agent, for example, silicone; pigments; pigment dispersents, corrosion inhibitors, for example, chromate pigments, numerous of all of which are known to the skilled of the art, may be employed in the coating compositions of the invention.

According to another aspect of the invention, a coating on a substrate is provided, which coating comprises the chain-extended, crosslinked polymer product following cure of a coating comprising the resin system of the invention. The coating composition can be a low solids composition, that is, it can have a high VOC, but generally a high solids composition, that is, one having a low VOC, is preferred for the reasons given above. It can be applied by any conventional method, including brushing, dipping, flow coating, spraying, etc. Spraying will generally be preferred, for example, for applying the composition as an automotive vehicle body primer or topcoat. In such spraying applications, the coating compositions of the invention are especially advantageous for use as high solids compositions.

Curing the coating composition requires baking for sufficient time at sufficiently elevated temperature to decompose the tertiary alcohol-blocked isocyanate functionality of the diblocked diisocyanate diurea oligomers to generate amine functionality and to promote the subsequent chain-extension and crosslinking reactions. The time and temperature required to cure the coating are interrelated and depend, in part, upon the particular diblocked diisocyanate diurea oligomer, polyepoxide, solvent and other materials, if any, used in the coating composition and upon the relative proportion of each. Employing a volatile organic content of about 360 g/l and selecting preferred components as described above, the required bake time and temperature is typically about 20 to 30 minutes at about 150° C. to about 180° C.

It is a significant advantage of the coating compositon of the invention that it does not require the addition of crosslinking agent. Known high solids coating compositions employing melamine crosslinking agent, for example, are disadvantaged by the cost of same and are further disadvantaged by the problems associated with the possible evolution of formaldehyde during cure of such coating compositions. It is another advantage of the invention, that the crosslink density can be easily controlled to a large extent, notwithstanding that a crosslinking agent is not added to the coating composition of the invention. As indicated above, the molecular weight and carbon chain lengths of the polyepoxide and of the reactants for preparation of the diblocked diisocyanate diurea oligomers of the invention can be selected to provide the desired crosslink density in the cured coating. In addition, the number of epoxy groups per polyepoxide molecule affords control of the crosslink density in the cured coatings.

High solids coating compositions according to the present invention, have been found to afford cured coatings with good humidity and solvent resistance and with exceptionally good corrosion resistance. The corrosion resistance has been found to be comparable and even better than that of conventional epoxy ester based, low solids sprayable coating compositions. The significant reduction in volatile organic content provided by the high solids coating composition of the invention can be seen to present, therefore, a highly advantageous advance in the art. Thus, for example, cured coatings according to the invention have been found to provide excellent corrosion resistance when applied over a metallic substrate such as, for example, when applied as an automotive vehicle primer coat over bare sheet steel.

While not wishing to be bound by theory, it is presently understood that, upon curing the coating composition of the invention the oligomer de-blocks, that is, each of the two tertiary carbamate moieties of the oligomer undergoes thermal decomposition, to generate a free amine group through elimination of carbon dioxide and an alkene. Each of these two amine groups of the "de-blocked" or thermally decomposed oliogmer is then available to react with the epoxy functionality of the polyepoxide to cure the resin. More specifically, each of the amine groups provides two active hydrogens for crosslinking and chain-extension polymerization reaction with an epoxide group. Thus, taking t-butanol-blocked oligomer as an example, it is believed that exposing the resin system to cure temperature would generate two free amine functionality on the oligomer through elimination of carbon dioxide and isobutylene. The free amine would then react with epoxide functionality to form a cured coating comprising a crosslinked, chain-extended epoxy/amine network. According to this understanding, the cured coating comprises β-hydroxy amine C-N linkages. Since each oligomer provides at least four active hydrogen, (two at each amine functionality) the resin system is self-crosslinking even if the polyepoxide consists entirely of diepoxide. The resin system does not require the addition of a crosslinking agent such as, for example, an aminoplast crosslinking agent. It will be appreciated, however, that by varying the epoxide functionality of the polyepoxide or by varying the ratio of diepoxide to higher polyepoxide, the degree of crosslinking in the cured coating can be controlled and, hence, to a large extent the properties of the coating, for example, flexability, can be controlled. The selection of polyepoxide(s) will depend upon the intended application of the particular coating composition.

While not wishing to bound by theory, the exceptional corrosion resistance provided by the invention is believed to stem, in part, from the presence in the cured coating of the urea linkages of the oligomer and, in part, from the presence of the C-N bonds of the β-hydroxy amine linkages formed by chain-extension and crosslinking reaction between epoxy functionality of the polyepoxide and free amine functionality of the oligomer generated during curing of the coating composition by the thermal decomposition of the tertiary alcohol-blocked isocyanate moieties of the oligomers. In addition, the absence of ester linkages in the cured coating is believed to improve corrosion resistance. Ester linkages are known to be attacked by hydroxide, a product of the metal corrosion process. In contrast, the urea linkages and the carbon-nitrogen bonds of the cured coating of the invention are believed to be more highly alkali resistant and thus highly resistant to degradation processes involving hydrolysis by cathodicly generated hydroxide, including, hydroxide generated by the corrosion of a metal substrate. Accordingly, the coating compositions of the invention provide improved corrosion resistance in comparison to known coating compositions, for example, those comprising ester or even urethane linkages. Thus, for example, automotive vehicle primers comprising the coating composition of the invention and having a calculated volatile organic content of 350–390 g/l, have been discovered to provide corrosion resistance far superior to that provided by typical low solids, e.g., greater than 500 g/l volatile organic content, epoxy ester-based primers.

It is preferred that the tertiary alcohol-blocked isocyanate groups and two of the epoxy of the polyepoxide each be an end group. Reactions between such epoxy end groups and de-blocked isocyanate end groups are believed to provide most efficient chain-extension during cure.

EXAMPLE I

Preparation of Half-blocked Diisocyanate

Blocking agent t-butanol, 74.g, in 10 g methyl amyl ketone is added to isphorone diisocyanate, 222.g, with 0.74 g dibutyl tin dilaurate in74 g methyl amyl ketone, at 35°–45° C. After addition of the alcohol, the reaction temperature is maintained at 35°–45° C. for about 48 hours. The resulting half-blocked aliphatic diisocyanate was cooled to room temperature and stored. The product was characterized by its infrared spectrum (after solvent evaporation) which showed isocyanate absorption and urethane absorption of approximately equal intensity.

EXAMPLE II

Preparation of Diblocked Diisocyanate Diurea Oligomer

The diblocked diisocyanate diurea oligomer is prepared by adding 75.g of the alcohol half-blocked aliphatic diisocyanate prepared in Example I to 11.6 g of 1,6-hexanediamine in 40.g of Hexyl Cellosolve Acetate. The rate of addition is controlled to maintain a gentle reflux. The reaction is stirred after completion of the addition for approximately 2 hours at 60° C. and then cooled to room temperature and stored. Infrared spectroscopy shows no absorption for isocyanate by the product.

EXAMPLE III

Preparation of Coating Compositon of the Invention

An automotive vehicle primer comprising a coating composition according to the invention is prepared by mixing a pigment package and a resin package, the following:

Pigment Package

| | |
|---|---|
| Silica | 23.6 g |
| Barytes | 21.4 g |
| Carbon black | .3 g |
| Titanium dioxide | 5.8 g |

Resin Package

| | |
|---|---|
| Diblocked diisocyanate diurea oligomer[1] | 35. g |
| Epon 829[2] | 20. g |
| Hexyl Cellosolve Acetate[3] | 35. g |
| Dibutyl tin dilaurate | .4 g |

[1] The oligomer is prepared as described in Example II.
[2] Epon 829 is a trademark of Shell Chemical Company, Houston, Texas, for Bisphenol A epichlorohydrin epoxy resin.
[3] Hexyl Cellosolve Acetate is a trademark of Union Carbide Corporation, New York, New York for organic solvent.

The pigment package is thoroughly dispersed into the binder package. The resulting composition is ready for use as an automotive primer. It has a calculated volatile organic content of about 370 g/l, and a viscosity of less than about 40 sec., #4 Ford Cup, at 27° C.

EXAMPLE IV

Preparation of Cured Coating

The coating composition of Example III is filtered, sprayed onto Parker cold rolled bare unpolished steel panels and baked at 180° C. for 30 minutes. The resulting cured coating has excellent solvent and humidity resistance and little or no scribe line associated adhesion loss after 24 hours salt spray exposure according to ASTM test method B117 using a Singleton SCCH Corrosion test cabinet operated at 35°±2° C.

EXAMPLE V

This example illustrates the preparation of a diblocked diisocyanate diurea oligomer suitable for use in the coating composition of the present invention.

A. Preparation of Half-blocked Diisocyanate

Alcohol half-blocked aliphatic diisocyanate is prepared according to the procedure of Example I.

B. Preparation of Diblocked Diisocyanate Diurea Oligomer

The diblocked diisocyanate diurea oligomer is prepared by adding 75.g of the alcohol half-blocked aliphatic diisocyanate prepared in Part A to 17.0 g of isophorone diamine in 40.g Hexyl Cellosolve Acetate. The ratio of addition is controlled to maintain a gentle reflux. The reation is stirred after completion of the addition for approximately two hours at 60° C. and then cooled to room temperature and stored. Infrared spectroscopy shows no absorption for isocyanate by the product.

EXAMPLE VI

Preparation of Coating Composition of the Invention

An automotive vehicle primer comprising a coating composition of the invention is prepared by mixing a pigment package and a resin package as follows:

Pigment Package

| | |
|---|---|
| Silica | 23.6 g |
| Barytes | 21.4 g |
| Carbon black | .3 g |
| Titanium dioxide | 5.8 g |

Resin Package

| | |
|---|---|
| Diblocked diisocyanate urea urethane oligomer[1] | 30. g |
| Epon 829[2] | 20. g |
| Hexyl Cellosolve Acetate[3] | 35. g |
| Dibutyl tin dilaurate | .4 g |

[1] Prepared as described in Example V.
[2] Epon 829 is a trademark of Shell Chemical Company, Houston, Texas, for a Bishenol A epichlorohydrin epoxy resin.
[3] Hexyl Cellosolve Acetate is a trademark of Union Carbide Corporation, New York, New York for organic solvent.

The pigment package is thoroughly dispersed into the binder package. The resulting composition is ready for use as an automotive primer. It has a calculated volatile organic content of about 370 g/l, and a viscosity of less than 40 sec., #4 Ford Cup, at 27° C.

EXAMPLE VII

Preparation of Cured Coating

The coating compositon of Example VI is filtered and sprayed on bare, unpolished steel panels and baked at 180° C. for 30 minutes. The resulting cured coating has excellent solvent and humidity resistance and shows little or no scribe line associated adhesion loss after 24 hours salt spray exposure according to ASTM test method B117 using a Singleton SCCH Corrosion test cabinet operated at 35°±2° C.

Particular embodiments of the present invention described above are illustrative only and do not limit the scope of the invention. It wil be apparent to the skilled of the art in view of the foregoing disclosure that modifications and substitutions can be made without departing from the scope of the invention.

I claim:

1. A chain-extendable, crosslinkable tertiary alcohol-diblocked diisocyanate diurea oligomer of number average molecular weight about 300 to about 5000 comprising the reaction product of diamine of molecular weight about 50 to about 700, with half-blocked organic diisocyanate of molecular weight about 120 to about 2000 in molar ratio of about 1:2, respectively, said half-blocked organic diisocyanate comprising the reaction product of an alcohol blocking agent bearing a tertiary hydroxyl group, with organic diisocyanate in molar ratio of about 1:1, said oligomer having a de-blocking temperature of about 80° C. to about 220° C.

2. The chain-extendable, crosslinkable tertiary alcohol-diblocked diisocyanate diurea oligomer of claim 1 wherein said oligomer has a number average molecular weight of about 300 to about 1500.

3. The chain-extendable, crosslinkable tertiary alcohol-diblocked diisocyanate diurea oligomer of claim 1 wherein said oligomer has a deblocking temperature of about 110° C. to about 180° C.

4. The chain-extendable, crosslinkable tertiary alcohol-diblocked diisocyanate diurea oligomer of claim 1 wherein said diamine comprises alkylenediamine wherein the alkylene moiety is straight or branched chain and has about 2 to about 20 carbons.

5. The chain-extendable, crosslinkable tertiary alcohol-diblocked diisocyanate diurea oligomer of claim 4 wherein said diamine bears two terminal amine group.

6. The oligomer of claim 5 wherein said diamine is selected from the group consisting of 1,6-hexanediamine, 1,5-pentanediamine, 1,4-butanediamine and a mixture of any of them.

7. The chain-extendable, crosslinkable tertiary alcohol-diblocked diisocyanate diurea oligomer of claim 1 wherein said diamine comprises cycloaliphatic diamines of about 4 to about 20 carbons or a mixture of them.

8. The chain-extendable, crosslinkable tertiary alcohol-diblocked diisocyanate diurea oligomer of claim 7 wherein said diamine is isophorone diamine.

9. The chain-extendable, crosslinkable tertiary alcohol-diblocked diisocyanate diurea oligomer of claim 1 wherein said diamine comprises aromatic diamine wherein each amine is substituted on the same benzene ring or on different benezene rings linked through a covalent bond or through one or more carbons of a one to seven carbon aliphatic moiety.

10. The chain-extendable, crosslinkable tertiary alcohol-diblocked diisocyanate diurea oligomer of claim 9 wherein said diamine is selected from the group consisting of toluene diamine, 4,4'methylenedianiline and a mixture of them.

11. The chain-extendable, crosslinkable tertiary alcohol-diblocked diisocyanate diurea oligomer of claim 10 wherein said diamine consists of toluene diamine.

12. The chain-extendable, crosslinkable tertiary alcohol-diblocked diisocyanate diurea oligomer of claim 1 wherein said tertiary alcohol is selected from the group consisting of t-butanol, 2-methyl-2-hydroxybutane, 2-methyl-2-hydroxypentane, 2-methyl-2-hydroxyhexane, 1-methylcyclohexanol and a mixture of any of them.

13. The chain-extendable, crosslinkable tertiary alcohol-diblocked diisocyanate diurea oligomer of claim 1 wherein said tertiary alcohol has about four to about 20 carbons.

14. The chain-extendable, crosslinkable tertiary alcohol-diblocked diisocyanate diurea oligomer of claim 1 wherein said organic diisocyanate is selected from phenylene diisocyanate, toluene diisocyanate, isophorone diisocyanate, diisocyanatoalkane wherein the alkylene moiety has about 3 to about 10 carbons and a mixture of any of them.

15. A solvent based resin composition comprising:
A. a chain-extendable, crosslinkable tertiary alcohol-diblocked diisocyanate diurea oligomer of number average molecular weight about 300 to about 5000 comprising the reaction product of diamine of molecular weight of about 50 to about 700, with half-blocked organic diisocyanate of molecular weight about 120 to about 2000 in molar ratio of about 1:2, respectively, said half-blocked organic diisocyanate comprising the reaction product of an alcohol of 4 to 20 carbons bearing a tertiary hydroxyl group, with organic diisocyanate in molar ratio of about 1:1, said oligomer having de-blocking temperature of about 80° C. to about 220° C.;
B. polyepoxide having 2 to about 10 epoxide groups and having a molecular weight of about 100 to about 1000, in weight ratio to said oligomer of about 1:1 to about 1:10; and
C. organic solvent.

16. The resin composition of claim 15 wherein said oligomer has a number average molecular weight of about 300 to about 1500.

17. The resin composition of claim 15 wherein said oligomer has a deblocking temperature of about 110° C. to about 180° C.

18. The resin composition of claim 15 wherein said diamine comprises alkylenediamine wherein the alkylene moiety is straight or branched chain and has about 2 to about 20 carbons.

19. The resin composition of claim 18 wherein said diamine bears two terminal amine group.

20. The resin composition of claim 19 wherein said diamine is selected from the group consisting of 1,6-hexanediamine, 1,5-pentanediamine, 1,4-butanediamine and a mixture of any of them.

21. The resin composition of claim 15 wherein said diamine comprises cycloaliphatic diamines of about 4 to about 20 carbons or a mixture of them.

22. The resin composition of claim 21 wherein said diamine is isophorone diamine.

23. The resin composition of claim 15 wherein said diamine comprises aromatic diamine wherein each amine is substituted on the same benzene ring or on different benzene rings linked through a covalent bond or through one or more carbons of a one to seven carbon aliphatic moiety.

24. The resin composition of claim 23 wherein said diamine is selected from the group consisting of toluene diamine, 4,4'methylenedianiline and a mixture of them.

25. The resin composition of claim 15 wherein said tertiary alcohol is selected from the group consisting of t-butanol, 2-methyl-2-hydroxybutane, 2-methyl-2-hydroxypentane, 2-methyl-2-hydroxyhexane, 1-methylcyclohexanol and a mixture of any of them.

26. The resin composition of claim 15 wherein said tertiary alcohol has about four to about 20 carbons.

27. The resin composition of claim 15 wherein said organic diisocyanate is selected from phenylene diisocyanate, toluene diisocyanate, isophorone diisocyanate, diisocyanatoalkane wherein the alkylene moiety has about 3 to about 10 carbons and a mixture of any of them.

28. The resin composition of claim 15 wherein said polyepoxide has 2 to about 4 epoxide groups.

29. The resin composition of claim 15 wherein said polyepoxide bears two terminal epoxide groups.

30. The resin composition of claim 15 wherein said polyepoxide comprises diepoxide.

31. The resin composition of claim 30 wherein said diepoxide is selected from the group consisting of 1,4-butanediol diglycidyl ether, 4-vinylcyclohexenedioxide, Bisphenol A epichlorohydrin epoxy resin, cycloaliphatic diepoxy resin, hydantoin epoxy resin, epoxy novalak resin and a mixture of any of them.

32. The resin composition of claim 15 wherein said oligomer and said polyepoxide are present in molar equivalent ratio of about 1:1 to about 2:1.

33. The resin composition of claim 15 wherein said organic solvent is selected from the group consisting of butanol, methyl ethyl ketone, methyl amyl ketone and a mixture of any of them.

34. A solvent based resin composition comprising:
A. the reaction product of diamine selected from the group consisting of 1,6-hexanediamine, 1,5-pentanediamine, 1,4-butanediamine, isophorone diamine, toluene diamine, methylenedianiline and a mixture of any of them, with half-blocked organic diisocyanate in molar ratio of about 1:2, respectively, said half-blocked organic diisocyanate comprising the reaction product of tertiary butanol with an approximately equal molar amount of organic diisocyanate of molecular weight less than about 250, said oligomer having a number average molecular weight of about 300 to about 1500 and de-blocking temperature of about 110° C. to about 180° C.;

B. polyepoxide of molecular weight about 300 to about 700, in weight ratio to said oligomer of about 1:1 to about 1:2, respectively; and C. organic solvent in such amount that said resin composition has a volatile organic content (calculated) of less than about 400 g/l.

35. The resin composition of claim 34 wherein said organic diisocyanate is selected from the group consisting of toluene diisocyanate, phenylene diisocyanate, isophorone diisocyanates, diisocyanatoalkane wherein the alkylene moiety has about 3 to about 10 carbons and a mixture of any of them.

36. A method of making a corrosion, humidity and solvent resistant coating in situ, on the surface of a substrate, which method comprises applying to said surface a solvent based resin composition comprising:

A. a chain-extendable, crosslinkable tertiary alcohol-diblocked diisocyanate diurea oligomer of number average molecular weight of about 300 to about 5000 comprising the reaction product of diamine of molecular weight about 50 to about 700, with half-blocked organic diisocyanate of molecular weight about 120 to about 2000 in molar ratio of about 1:2, respectively, said half-blocked organic diisocyanate comprising the reaction product of an alcohol blocking agent bearing a tertiary hydroxyl group, with organic diisocyanate in molar ratio of about 1:1, said oligomer having de-blocking temperature of about 80° C. to about 220° C.;

B. polyepoxide having about 2 to about 10 epoxide groups and having a molecular weight of about 100 to about 1000, in weight ratio to said oligomer of about 1:1 to about 1:10; and C. organic solvent; and heating said composition at about 80° C. to about 220° C. for a time sufficient to cure said composition.

37. A corrosion, humidity and solvent resistant coating made, in situ, on the surface of a substrate according to the method of claim 36.

* * * * *